United States Patent [19]

Carter et al.

[11] Patent Number: 5,731,399
[45] Date of Patent: Mar. 24, 1998

[54] DI- AND POLYAMINO COMPOUNDS FOR USE IN THE PREPARATION OF POLYURETHANES

[75] Inventors: Steve Carter, Lancashire, United Kingdom; Gonda Van Essche, Worms, Germany

[73] Assignee: Imperial Chemical Industries PLC, London, England

[21] Appl. No.: 573,792

[22] Filed: Dec. 18, 1995

Related U.S. Application Data

[62] Division of Ser. No. 61,146, May 13, 1993, abandoned.

[30] Foreign Application Priority Data

Feb. 8, 1993 [GB] United Kingdom ............... 9302418

[51] Int. Cl.⁶ .................................................. C08G 18/48
[52] U.S. Cl. .................. 528/79; 252/182.2; 252/182.27; 252/182.34; 528/70; 528/68; 528/67; 560/359; 564/330; 564/346
[58] Field of Search .................. 252/182.2, 182.27, 252/182.34; 528/79, 70, 68, 67; 560/359; 564/346, 330

[56] References Cited

U.S. PATENT DOCUMENTS

| | | | |
|---|---|---|---|
| 3,654,364 | 4/1972 | Meckel et al. | 564/305 |
| 4,218,543 | 8/1980 | Weber et al. | 521/51 |
| 4,231,964 | 11/1980 | Kuhne et al. | 564/305 |
| 4,769,439 | 9/1988 | Talley et al. | 528/126 |

FOREIGN PATENT DOCUMENTS

| | | |
|---|---|---|
| 2904124 | 8/1980 | Germany . |
| 4284455 | 10/1992 | Japan . |
| 0598877 | 3/1977 | U.S.S.R. . |
| 2068379 | 8/1981 | United Kingdom . |

OTHER PUBLICATIONS

J.H. Saunders & K.C. Frisch; Polyurethanes; 1962; p. 18.

Avadhani, C. V., Wadgaonkar, P. P., and Vernekar, S. P., Synthesis and *Characterization of Formal–Group–Containing Diisocyanates and Polyimides Therefrom*, Journal of Applied Polymer Science, Vo. 45, 1335–1340 (1992).

"Methylenation of Phenols", Fujita et al., *Journal of the Chemical Society of Japan*, Nippon Kagaku Kaishu, 1975, (Abstract).

*Chemical Abstracts*, 112: 178929d., 1990.

*Chemical Abstracts*, 113: 193912g. 1990.

P. W. Wajtkowski, "Aromatic–Aliphatic Azomethine Ether Polymers and Fibers;"Macromolecules; vol. 20, No. 4, Apr. 1987, pp. 740–748.

R. F. Brown, "Organic Chemistry", 1975, p. 491.

*Primary Examiner*—Rachel Gorr

[57] ABSTRACT

Compounds are disclosed which correspond to general formula (I)

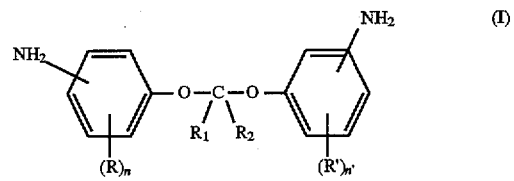

wherein:

R and R' each independently represent an alkyl chain of 1 to 10 carbon atoms, which may be branched, and which may be partially or fully fluorinated;

n and n' each independently represent an integer of from 0 to 4, the R, respectively R' substituents may be the same or different when n, respectively n' is greater than 1;

$R_1$ and $R_2$ independently represent hydrogen or an alkyl chain of 1 to 5 carbon atoms, which may be branched, and which may be partially or fully fluorinated, or $R_1$ and $R_2$ together represent an alkylene chain of 2 to 6 carbon atoms, which may be substituted by alkyl groups and which may be partially or fully fluorinated;

and wherein the amino substituents are situated in ortho, meta or para position with regard to the oxy substituent;

with the proviso that said compound does not correspond to bis-(2- and 3- and 4-aminophenoxy)methane.

26 Claims, No Drawings

DI- AND POLYAMINO COMPOUNDS FOR USE IN THE PREPARATION OF POLYURETHANES

CROSS REFERENCE TO RELATED APPLICATIONS

The present application is a divisional of U.S. patent application Ser. No. 08/061,146 filed May 13, 1993 entitled "Novel Di- and Polyamino Compounds for Use in the preparation of Polyurethanes", now abandoned.

The present invention relates to novel compounds that can be used for preparing polyols and polyisocyanates, which in turn can be used in the synthesis of polyurethanes. The present invention relates also to the polyols, polyisocyanates and polyurethanes obtained by using said compound.

It is well known to manufacture polyurethane materials of a cellular or non-cellular, flexible or rigid nature by reacting organic polyisocyanates having two or more isocyanate groups per molecule with compounds containing a plurality of isocyanate reactive groups, for example polyols and polyamines, in the presence, where required, of other components such as blowing agents, cross-linking agents, catalysts and surfactants. These polyurethane materials may take the form of adhesives, coatings, elastomers, fibres, films, foams, thermoplastics and the like.

Polyols for use in preparing polyurethanes are usually prepared by reacting an initiator compounds having a plurality of active hydrogen atoms (alcohols or amines) with an alkylene oxide (usually propylene oxide). A suitable initiator compound is diaminodiphenylmethane (methylenedianiline). Polyamines for use in preparing polyurethanes are obtained by converting the hydroxyl end-groups of the polyols to amino end-groups.

Organic polyisocyanates for use in preparing polyurethanes are conventionally manufactured by reacting phosgene with the corresponding organic polyamines. Thus the starting materials for diisocyanatodiphenylmethane (MDI) and its homologues, are the mixtures of isomers and homologues of diaminodiphenylmethane that are formed by the condensation reaction of formaldehyde and aniline.

We have now found novel diamino compounds suitable for use in the preparation of polyols and polyisocyanates, and thus also polyurethanes.

Thus according to the present invention compounds corresponding to general formula (I) are provided:

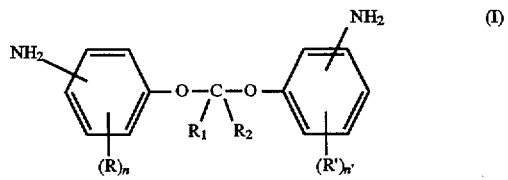

wherein:

R and R' each independently represent an alkyl chain of 1 to 10 carbon atoms, which may be branched, and which may be partially or fully fluorinated;

n and n' each independently represent an integer of from 0 to 4, the R, respectively R' substituents may be the same or different when n, respectively n' is greater than 1;

$R_1$ and $R_2$ independently represent hydrogen or an alkyl chain of 1 to 5 carbon atoms, which may be branched, and which may be partially or fully fluorinated, or $R_1$ and $R_2$ together represent an alkylene chain of 2 to 6 carbon atoms, which may be substituted by alkyl groups and which may be partially or fully fluorinated; and wherein the amino substituents are situated in ortho, meta or para position with regard to the oxy substituent; with the exception of bis-(2- and 3- and 4-aminophenoxy) methane.

Bis-(4-aminophenoxy)methane (compound of formula (I) wherein $R_1$ and $R_2$ both represent hydrogen, n and n' both are 0 and wherein the amino substituents are in para position) has been described in SU 598877 for use in polyamide synthesis. Bis-(2- and 3- and 4-aminophenoxy) methane have been described in DE 2904124 for use in the synthesis of bisazo dyes. The use of these compounds in polyols, polyisocyanate and polyurethane synthesis has not been described hitherto. Further the unsubstituted bis-(aminophenoxy)methane compounds have the disadvantage of being insoluble in the solvents commonly used in polyol and polyisocyanate production.

Preferably at least one of the $R_1$, $R_2$, R and R' substituents, and preferably at least one of the R and R' substituents, represents an alkyl chain (for example methyl or t-butyl). In that case the solubility of the compound according to formula (I) is improved. Other preferred compounds are those wherein $R_1$ and $R_2$ together represent an alkylene chain, preferably of 5 carbon atoms, also for solubility reasons.

Preferred compounds according to formula (I) are listed below in table 1.

TABLE 1

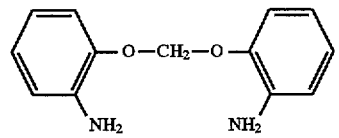 I.1

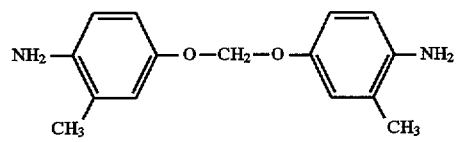 I.2

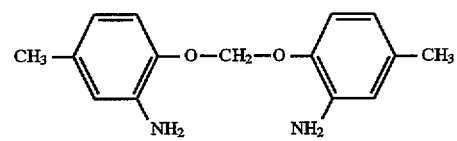 I.3

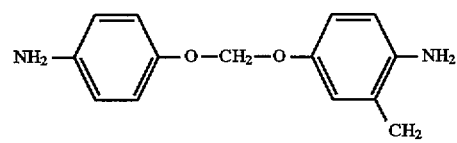 I.4

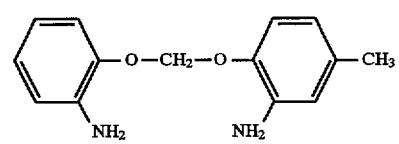 I.5

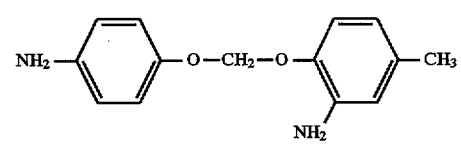 I.6

TABLE 1-continued

| | |
|---|---|
| I.7 | (structure: NH₂-phenyl(CH₃)-O-CH₂-O-phenyl(NH₂)-CH₃) |
| I.8 | (structure: NH₂-phenyl-O-CH₂-O-phenyl-NH₂) |
| I.9 | (structure: (CH₃)₃C-phenyl(NH₂)-O-CH₂-O-phenyl(NH₂)-C(CH₃)₃) |
| I.10 | (structure: (CH₃)₃C-phenyl(NH₂)-O-CH₂-O-phenyl(NH₂)(CH₃)) |
| I.11 | (structure: (CH₃)₃C-phenyl(NH₂)-O-CH₂-O-phenyl-NH₂) |
| I.12 | (structure: (CH₃)₃C-phenyl(NH₂)-O-CH₂-O-phenyl(NH₂)-CH₃) |
| I.13 | (structure: (CH₃)₃C-phenyl(NH₂)-O-CH₂-O-phenyl-NH₂) |
| I.14 | (structure: NH₂-phenyl(CH₃)-O-C(cyclohexyl)-O-phenyl(CH₃)-NH₂) |
| I.15 | (structure: NH₂-phenyl(CH₃,CH₃)-O-CH₂-O-phenyl(CH₃,CH₃)-NH₂) |
| I.16 | (structure: CH₃-phenyl(CH₃,NH₂)-O-CH₂-O-phenyl(CH₃,NH₂)-NH₂) |

The compounds according to formula (I) wherein $R_1$ and $R_2$ both represent hydrogen are prepared by reacting the corresponding (substituted) aminophenol(s) with methylenechloride under basic conditions. Methods for performing this reaction are known in the art and are described in Chemistry Letters, 1988, pages 1773 to 1776. When the two aminophenols are different then mixtures of compounds according to formula (I) are obtained.

The compounds according to formula (I) wherein $R_1$ and $R_2$ do not both represent hydrogen are prepared by reacting the corresponding (substituted) nitrophenol(s) with the corresponding substituted ketone or aldehyde under acid conditions followed by reduction of the nitro groups (for example, by Pd(C) under hydrogen atmosphere). Alternatively the corresponding (substituted) aminophenols of which the amino group has been protected (for example, by reaction with chloroformate methyl ester) is reacted with the corresponding ketone or aldehyde followed by deprotection of the amino group (for example, by reaction with methanol). These preparation methods are known in the art and are described in, for example, "Vogels textbook of Practical Organic Chemistry", fifth Edition 1989, John Wiley & Sons Inc., New York and in "Protective Groups in Organic Synthesis" by T. W. Greene, John Wiley & Sons Inc., New York, 1981.

Therefore the present invention also provides a method for preparing compounds according to formula (I) wherein $R_1$ and $R_2$ both represent hydrogen with the exception of bis-(2- and 3- and 4-aminophenoxy)methane by reacting a compound of formula (II) and/or a compound of formula (III) with methylenechloride ($CH_2Cl_2$) under basic conditions

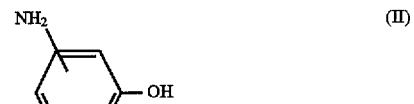

(II)

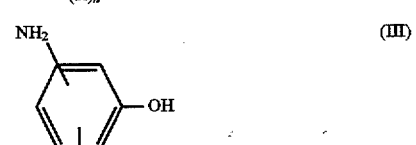

(III)

wherein R, n, R' and n' have the same meanings as hereinbefore for the compounds of formula (I).

The present invention also provides a method for preparing compounds according to formula (I) wherein $R_1$ and $R_2$ do not both represent hydrogen comprising the steps of a) reacting a compound of formula (IV) and/or a compound of formula (V) with a compound of formula (VI) under acid conditions

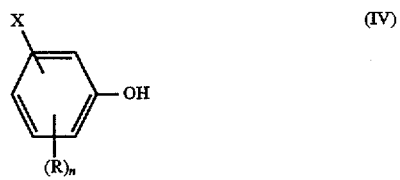

(IV)

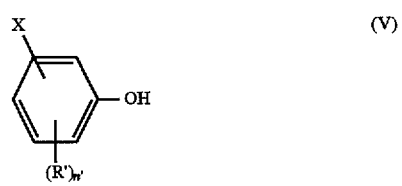

(V)

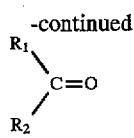

wherein R, n, R' and n' have the same meanings as hereinbefore for the compounds of formula (I), and wherein X represents a nitro group or a protected amino group;

b) reducing the nitro groups into amino groups in case X represents a nitro group, or deprotecting the amino group if X represents a protected amino group.

Compounds according to formula (I) are useful in the preparation of polyurethanes. They can be used as such and have the function of, for example, amine chain extenders (especially in flexible foam applications) or they can be converted into polyols and/or polyisocyanates which in turn can be converted into polyurethanes.

Therefore the present invention also provides polyol compositions obtainable by oxyalkylation of a compound of formula (I) and optionally a second initiator.

The polyol compositions according to the present invention may contain oxyalkylene units derived solely from propylene oxide or, alternatively, units derived from both propylene and ethylene oxides may be present. In the latter case it is preferred that the ethylene oxide content does not exceed 70% of the total alkylene oxide units on a molar basis. When both propylene and ethylene oxides are employed in the oxyalkylation, they may be reacted either simultaneously or sequentially with the compound according to formula (I).

In conjunction with the compound of formula (I) another initiator may be used in the formation of the polyol compositions according to the present invention.

Suitable co-initiators include: water and polyols, for example ethylene glycol, propylene glycol and their oligomers, glycerol, trimethylolpropane, triethanolamine, pentaerythritol, sorbitol and sucrose; polyamines, for example ethylene diamine, tolylene diamine, diaminodiphenylmethane and polymethylene polyphenylene polyamines; and aminoalcohols, for example ethanolamine and diethanolamine; and mixtures of such initiators. Preferred co-initiators are the bi- and trifunctional ones such as diethylene glycol and glycerol.

The co-initiator can be used in varying ratios but generally 10 to 40 parts of co-initiator are used for 100 parts of initiator according to the invention.

Polyols having hydroxyl values in the range 30 to 880 mg KOH/g can be prepared, preferably in the range 30 to 620 mg KOH/g and more preferably in the range 300 to 500 mg KOH/g.

The method for making the polyol compositions according to the present invention basically follows prior art modes of making polyether polyols.

The oxyalkylation is performed in the presence of ionic catalysts as known in the art. The amount of catalyst utilised may vary over a wide weight percentage based on the weight of the initiator(s). Usually an amount of catalyst ranging from about 0.01 to about 5 weight % is employed, based on the weight of the initiator. More often, the amount employed is 0.1–2%, and most often is 0.3–1%. Usually basic catalysts are used. Potassium hydroxide or sodium hydroxide are most preferred. Other metal hydroxides (such as cesium hydroxide) or tertiary amines can also be used. Acid catalysis is also possible. Lewis-acids like boron trifluoride, stannic chloride, or combinations of ferric chloride with thionyl chloride are preferred.

The amount of alkylene oxide added to the compound of formula (I) and the optional co-initiator may range over a wide range of about 1–100 moles of alkylene oxide per mole of initiator. More often, 1–50 moles of alkylene oxide are reacted per mole of initiator.

The temperature of reaction may range from about 50° C. to about 200° C., and is preferably from 80° C. to 150° C.

Where the polyol compositions are intended for use in the preparation of rigid polyurethane foams, the polyols should have average hydroxyl numbers in the range from 300 to 880 mg KOH/g, especially in the range from 300 to 500 mg KOH/g, and a hydroxyl functionality in the range from 2 to 8, especially in the range from 3 to 6, preferably 4. When functionalities higher than 4 are needed a co-initiator containing from 5 to 8 active hydrogens per molecule should be used.

Where the polyol compositions are intended for use in the preparation of flexible foams, the polyols should have a molecular weight in the range from 1000 to 10000, preferably from 3000 to 7500, and a number average functionality in the range from 2 to 4. In that case a co-initiator is not really necessary; if one is used said co-initiator should contain from 2 to 4 active hydrogens per molecule.

The present invention also provides polyisocyanate compositions obtainable by phosgenation of compounds of formula (I) with the exception of bis-(3- or 4-isocyanatophenoxy)methane.

Thus according to the present invention there is provided a novel compound corresponding to formula (VII)

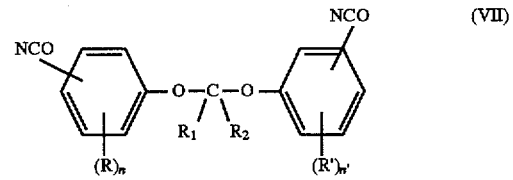

wherein R, n, R', n', $R_1$ and $R_2$ have the same meanings as given to them hereinbefore for the compounds of formula (I) and wherein the isocyanato substituents may be positioned in ortho, meta and para position, with the exception of bis-(3- or 4-isocyanatophenoxy)methane.

Bis-(3- and 4-isocyanatophenoxy)methane are described in the Journal of Applied Polymer Science, Vol. 45, 1992, pages 1335–1340. The use of this compound in the preparation of polyurethanes has not been described hitherto.

The phosgenation is performed according to methods generally known in the art. The phosgenation can take place both continuously and discontinuously. The phosgenation can take place in two steps according to the well-known cold/hot phosgenation principle or in one step according to the hot phosgenation principle. Inert organic compounds are used as solvent. Suitable solvents include aliphatic, cycloaliphatic and aromatic hydrocarbons, halogenated hydrocarbons, nitro-substituted hydrocarbons, aliphatic-aromatic ethers, aromatic ethers, carboxylic acid esters, carboxylic acid nitriles, sulfone, phosphoric acid halogenide and phosphoric acid ester. Chlorobenzene and ortho dichlorobenzene have been generally accepted as the most commonly used solvents. Further the phosgenation can take place at normal or slightly elevated pressure.

The phosgene is added to the composition in an amount of 1 to 10 times, in particular 1.05 to 6 times the stoichiometric amount. Catalysts such as dimethylformamide and acid acceptors such as pyridine can accelerate the phosgenation.

Further processing of the reaction mixture after the phosgenation involves the recovery of gaseous substances (hydrogen chloride and excess of phosgene) and multistage distillation to separate the solvent. The isocyanate itself can then be recovered by means of extraction, crystallisation, distillation or sublimation.

The isocyanates according to formula (VII) can be post-reacted; they can be trimerised, urea-modified, allophonate-modified, biuret-modified or they can be prepolymerised (i.e. reacted with polyols, etc.). In any of these forms they can then be used in the preparation of polyurethanes.

The compounds of the present invention according to general formula (I) can also be used in the production of modified diaminodiphenylmethane (DADPM) compounds.

Compounds of formula (I) can also be reacted with aniline and formaldehyde under acid conditions, typically aqueous hydrogen chloride, to yield compounds corresponding to formula (VIII), and isomers and homologues thereof.

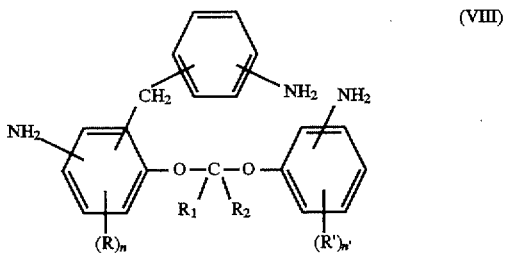

(VIII)

In that reaction also isomers and homologues of diaminodiphenylmethane are formed.

Compounds corresponding to formula (VIII) can be used in the pure form as chain extenders in the polyurethane forming process. They can also be converted into polyols and into polyisocyanates in the same way as described hereinbefore for the compounds corresponding to formula (I). Due to their higher functionality polyisocyanates obtained from compounds corresponding to formula (VIII) are more suitable in the preparation of rigid polyurethane foam than polyisocyanates derived from compounds corresponding to formula (I).

The polyol compositions and polyisocyanate compositions resulting from compounds according to formula (I) or from compounds according to formula (VIII) can be used in a conventional manner in order to prepare polyurethane materials. The polyurethane materials can be solid (e.g. elastomers) or they can be cellular. The polyurethane material can be in the form of rigid foams, flexible foams, self-skinning foams, elastomers, thermoplastic polyurethane (TPU) or as coatings, adhesives, sealants and binders.

The term "polyurethane" as used herein is meant to also include urethane-modified polyisocyanurate.

In general, polyurethane preparation involves reacting a polyol composition with an organic polyisocyanate in the presence of a foaming agent in the case of polyurethane foam preparation, and usually, catalysts, surfactants and other known additives.

A polyol composition according to the present invention may be reacted with a conventional polyisocyanate composition, or a polyisocyanate composition according to the present invention may be reacted with a conventional polyol composition. Alternatively a polyol composition according to the present invention may be reacted with a polyisocyanate composition according to the present invention. Further the polyol composition used may comprise a mixture of different types of polyols, including conventional polyols and polyols according to the present invention; similarly the polyisocyanate composition used may comprise a mixture of different types of polyisocyanates, including conventional polyisocyanates and polyisocyanates according to the invention.

Conventional polyisocyanates for use in the polyurethane forming process include aliphatic, cycloaliphatic, araliphatic and aromatic polyisocyanates as proposed in the literature. Of particular importance are aromatic diisocyanates such as tolylene and diphenylmethane diisocyanate in the well known pure, modified and crude forms, in particular the so-called MDI variants and the mixtures of diphenylmethane diisocyanate(s) and oligomers thereof known in the art as "crude" or "polymeric" MDI. The polyisocyanates used in the polyurethane forming process can be in the form of a prepolymer, or in the form of a trimerised isocyanate or a modified (urea, allophonate, biuret) isocyanate.

Preferred polyisocyanates for the preparation of rigid polyurethane foams are those having an average nominal functionality of 2.4–3.0 and in particular of 2.4–2.9.

Preferred polyisocyanates for the preparation of flexible and integral skin foams and for microcellular elastomers are those having an average nominal functionality of 2.0 to 2.4.

Foaming agents which may be used include carbon dioxide-evolving compounds such as water and inert low boiling compounds having a boiling point of above −70° C. at atmospheric pressure. Suitable inert blowing agents include those well known and described in the art, for example, hydrocarbons, dialkyl ethers, alkyl alkanoates, aliphatic and cycloaliphatic hydrofluorocarbons, hydrochlorofluorocarbons, chlorofluorocarbons, hydrochlorocarbons and fluorine-containing ethers.

Catalysts include the usual tertiary amines and tin compounds whilst useful surfactants include siloxane-oxyalkylene copolymers and conventional non-ionic types. Other useful additives include fire-retardants, for example, tris-2-chloroethyl phosphate and dimethyl methylphosphonate.

In operating the polyurethane forming process the known one-shot, full prepolymer or semi-prepolymer techniques may be used together with conventional mixing methods and the foams and elastomers may be prepared in the form of mouldings, cavity fillings, sprayed foam, frothed foam, slabstock foam or laminates with other materials such as hardboard, plasterboard, plastics, paper or metals.

It is convenient in many applications to provide the components for polyurethane production in pre-blended formulations based on each of the primary polyisocyanate and polyol components. In particular, many reaction systems employ a polyol formulation which contains the major additives such as the blowing agent and the catalyst in addition to the polyol component or components.

When the compounds according to formula (I) or (VIII) are used as chain extenders in the polyurethane forming process they are conveniently added to the pre-blended polyol formulation in an amount of from 0.1 to 20 parts by weight based on the total composition.

The polyurethanes derived from the polyol and/or polyisocyanate compositions according to the present invention show improved physical properties, in particular dimensional stability, improved fire performance, and improved thermal insulation ageing.

Further the solubility of the blowing agent is improved by using polyol compositions according to the present invention. And particularly when gaseous blowing agents are used the frothing effect is diminished.

The invention will be further illustrated with respect to the following specific examples, which are given by way of illustration and not as limitations on the scope of this invention.

EXAMPLE 1

Preparation of Bis(aminophenoxy/cresoxy)methanes

General Procedure

Dichloromethane (2.5 l), aminophenol and/or aminocresol (2.2 mole in total) and tetraethylammoniumbromide (0.5 mole) were introduced into a 5 l flask followed by addition of potassiumhydroxide (7.1 mole) with stirring in a nitrogen gas atmosphere. The mixture was subjected to condensation reaction under mild reflux for 20 hours. The temperature inside the reactor was about 40° C. After cooling down to room temperature water (500 ml) was added, followed by agitating the mixture and allowing it to stand for a while. Thereafter the dichloromethane layer was separated off, dichloromethane (150 ml) was added once again, the mixture was agitated and allowed to stand for a while, followed by separation of the dichloromethane layer. The dichloromethane layers were collected, dried over magnesium sulfate and filtered. The dichloromethane was evaporated under reduced pressure. Liquid products were obtained.

Compound I.3 was prepared along the lines of the above general procedure starting from 2.2 mole 2-amino-p-cresol. Yield was 99%. Compound I.3 was fully characterised by means of IR and NMR.

Starting from 1.1 mole of 4-amino-m-cresol and 1.1 mole of 4-aminophenol and following the above general procedure a mixture of the following compounds was obtained: 16% of bis-(4-aminophenoxy)methane, 46% of compound I.4 and 38% of compound I.2. Total yield was 97%. The amounts of the different compounds in the mixture was determined by means of gas chromatography. The compounds themselves were fully characterised by means of IR and NMR.

Starting from 1.1 mole of 2-aminophenol and 1.1 mole of 2-amino-p-cresol and following the above general procedure a mixture of the following compounds was obtained: 22% of compound I.1, 45% of compound I.5 and 28% of compound I.3.

Starting from 1.1 mole of 4-aminophenol and 1.1 mole of 2-amino-p-cresol and following the above general procedure a mixture of the following compounds was obtained: 31% of bis-(4-aminophenoxy)methane, 47% of compound I.6 and 22% of compound I.3.

Starting from 1.1 mole of 4-amino-m-cresol and 1.1 mole of 2-amino-p-cresol and following the above general procedure a mixture of the following compounds was obtained: compound I.2, compound I.7 and compound I.3.

Starting from 1.1 mole of 4-aminophenol and 1.1 mole of 2-aminophenol and following the above general procedure a mixture of the following compounds was obtained: bis-(4-aminophenoxy)methane, compound I.8 and compound I.1.

EXAMPLE 2

Conversion of Bis(aminophenoxy/cresoxy)methanes Into Polyols 2000 g of compound I.4 were introduced into a stainless steel pressure reactor equipped with cooling coils. The reactor was sealed, inert material was removed by vacuum and the reactor was three times purged with nitrogen. The reaction mixture was heated to 80° C., followed by the addition of 989 g of propylene oxide. The temperature was further increased to 110° C. and the batch was cooked down for 4 hours. A potassium hydroxide catalyst was mixed with an equal amount by weight of water and introduced into the reactor. Thereafter the total amount of 2942 g of propylene oxide was introduced into the reactor and the time recorded. After 12 hours 3% Ambosol (magnesium silicate sold by Hoechst) was charged and water was removed by vacuum over 4 hours. The polyol obtained was filtered through a plate filter, Properties of the obtained polyol are listed below:
functionality: 4
hydroxyl value: 310
acid value: 0.05 mg KOH/g
% water: 0.1
colour: 14–15 Gardner Units
Na: 27 ppm
K: 4 ppm
viscosity: 60 Poise at 50° C.

EXAMPLE 3

Conversion of Bis(aminophenoxy/cresoxy)methanes Into Polyisocyanates

Example 3.1

To a solution of 20 g phosgene in 100 ml of dry dioxane was added 20 g of compound I.2 in 200 ml of dry dioxane under vigorous stirring. The mixture was refluxed for one hour. After evaporation of the dioxane under reduced pressure the residue was extracted with 100 ml of hot cyclohexane. After cooling and filtration a light brown solid was obtained that was characterised by means of IR and NMR as being bis(4-isocyanato-m-cresoxy)methane. Yield was 67%. Melting point of the obtained product was 124° C.

Example 3.2

To a solution of 20 g phosgene in 100 ml of dry dioxane was added 20 g of a mixture of 22% of compound I.1, 50% of compound I.5 and 28% of compound I.3 in 200 ml of dry dioxane under vigorous stirring. The mixture was refluxed for two hours. After evaporation of the dioxane under reduced pressure the residue was extracted with 100 ml of hot cyclohexane. After cooling and filtration yellow crystals were obtained that were characterised by means of IR and NMR as being a mixture of bis(2-isocyanatophenoxy) methane (19%), (2-isocyanato-p-cresoxy)-(2-isocyanatophenoxy)methane (45%) and bis(2-isocyanato-p-cresoxy)methane (36%). Yield was 70%. Melting point of the obtained mixture was 83° C.

In an analogous manner as described above in examples 3.1 and 3.2 the following compounds were prepared:

bis(4-isocyanato-m-cresoxy)methane (melting point 123° C.) starting from compound I.2;

bis(2-isocyanato-p-cresoxy)methane (melting point 128° C.) starting from compound I.3;

a mixture (melting point 84° C. and 106° C.) of (4-isocyanatophenoxy)-(4-isocyanato-m-cresoxy) methane (41%), bis(4-isocyanatophenoxy)methane (4.3%) and bis(4-isocyanato-m-cresoxy)methane (55%) starting from a mixture of compound I.4, compound I.2 and bis(4-aminophenoxy)methane;

a mixture (melting point 131° C.) of (4-isocyanatophenoxy)-(2-isocyanato-p-cresoxy) methane (45%), bis(4-isocyanatophenoxy)methane (36%) and bis(2-isocyanato-p-cresoxy)methane (19%) starting from a mixture of compound I.6 (47%), compound I.3 (22%) and bis-(4-aminophenoxy)methane (31%);

a mixture (melting point 113° C.) of (4-isocyanato-m-cresoxy)-(2-isocyanato-p-cresoxy)methane, bis(4-isocyanato-m-cresoxy)methane and bis(2-isocyanato-p-cresoxy)methane starting from a mixture of compound I.7, compound I.2 and compound I.3.

EXAMPLE 4

Preparation of Modified DADPM Compounds

General Procedure

Aniline, a bis(aminophenoxy/cresoxy)methane (from 1 to 30% based on the aniline weight) (2.4 mole in total amines) and aqueous hydrochloric acid (0.5 mole) were mixed under stirring and heated to 45° C. Formaldehyde solution (1 mole formaldehyde) was added over a period of 40 minutes while maintaining the temperature at 45° C. The temperature was increased to 100° C. and the mixture was maintained at that temperature for 1 hour 30 minutes to ensure that the reaction was complete. The mixture was then neutralised with excess sodium hydroxide solution. The neutralised modified DADPM products were washed with water and the aniline was stripped off.

Following the above general procedure with 85 g (0.91 mole) aniline, 15 g (0.062 mole) of compound I.4, 21.5 g hydrochloric acid and 38.3 g of a 30% formaldehyde solution a reaction mixture was obtained with a diamine content of 45% (resulting from the formed diaminodiphenylmethane (DADPM) 4,4', 2,4' and 2,2' isomers and from the remaining (aminophenoxy)-(aminocresoxy)methane) and a viscosity of 3.5 Poise at 50° C. The presence of the acetal modified DADPM product was proven by means of NMR and GLC.

Starting from the bis(aminophenoxy/cresoxy)methane compounds identified below in table 2 in amounts identified below in table 2 and following the above general procedure acetal modified DADPM products were obtained. The diamine content and the DADPM isomer ratios and the remaining free bis(aminophemoxy/cresoxy)methane content are also listed below in table 2.

As comparative example a polyurethane foam (foam 2) was prepared having the same ingredients but using a DADPM based polyether polyol instead of the polyol according to the invention. The same properties were measured for the comparative foam. The results are also listed in table 3.

TABLE 3

|  | foam 2 | foam 1 |
| --- | --- | --- |
| deformation under load (%) | −29.0 | −10.0 |
| compression strength to rise | 188 | 242 |
| compression strength to width | 54 | 78 |
| dimensional stability after 1 day |  |  |
| −20 C. length | −1.5 | −0.2 |
| width | −2.4 | −0.2 |
| height | 0.0 | −0.3 |
| volume | −3.9 | −0.7 |
| 70 C. length | −0.3 | 0.2 |
| width | −0.4 | 0.5 |
| height | −0.2 | 0.0 |
| volume | −0.9 | 0.7 |

TABLE 2

| Starting compound | weight % based on aniline | % diamine | % DADPM isomer 4,4' | % DADPM isomer 2,4' | % DADPM isomer 2,2' | remaining of starting compound | viscosity (Poise) 500° C. |
| --- | --- | --- | --- | --- | --- | --- | --- |
| I.4 | 5 | 53 | 93.5 | 5.5 | 1 |  | 2 |
|  | 10 | 47 | 93 | 5.7 | 1.3 | 13.6 | 2.6 |
|  | 15 | 45 | 93.1 | 5.8 | 1.1 | 17.6 | 3.5 |
|  | 20 | 38 | 94.5 | 4.8 | 0.7 | 16 | 4.5 |
| I.5 | 5 | 51 | 92.9 | 6.1 | 1 |  | 4 |
|  | 10 | 47 | 92.8 | 6.0 | 1.2 | 0.1 | 4 |
|  | 15 | 43 | 93.4 | 5.6 | 1.0 | 0.1 | 10 |
|  | 20 | 37 | 93.6 | 5.7 | 0.7 | 3 | 20 |
| I.6 | 5 | 52 | 92.6 | 6.3 | 1.1 |  | 3.1 |
|  | 10 | 51 | 92.6 | 6.4 | 1.0 | 4.6 | 6.1 |
|  | 15 | 49 | 93.4 | 5.6 | 1.0 | 6.1 | 13 |
|  | 20 | 48 | 93.4 | 5.8 | 0.8 | 7 | 24 |

EXAMPLE 5

Synthesis of Polyurethane Foam

A polyol blend comprising 62.88 pbw of the polyol prepared in example 2, 20.94 pbw of a polyether polyol of hydroxyl value 440 and functionality 4.5 and 5 pbw of a polyether polyol of hydroxyl value 540 and functionality 3, 5.7 pbw of a triethylphosphate fire retardant, 0.89 pbw of a silicone surfactant (DC 193 sold by Dow Corning) and 3.05 pbw of a tertiary amine catalyst (DABCO 33 LV sold by Air Products), 2.5 pbw of water and 17 pbw of CFC 11 as blowing agent (ARCTON 11 supplied by Imperial Chemical Industries) were reacted with polymeric MDI (Suprasec VM 85 HF sold by Imperial Chemical Industries) under standard foam forming conditions and several properties of the resultant foam (foam 1) were determined. Deformation in % under a load of 0.04N for 2 days at 70° C. was determined. Compression strength (in kPa) in the foam rise direction and in the foam width direction was determined. Dimensional stability (in %) of the foam in the length, width, height and volume was determined after storage for 1 day or 15 days at −20° C. and at 70° C. A flame spread test (BS 4735 corresponding to ISO 3582) was performed. The thermal insulation value lambda (in mW/m K) was measured initially and after storage for 1 to 3 weeks at 70° C. The results are listed in table 3.

TABLE 3-continued

|  | foam 2 | foam 1 |
| --- | --- | --- |
| dimensional stability after 15 days |  |  |
| −20 C. length | −20.9 | −2.5 |
| width | −22.8 | −1.6 |
| height | −1.3 | 0.2 |
| volume | −45.0 | −3.9 |
| 70 C. length | −3.3 | 1.9 |
| width | 3.7 | 1.9 |
| height | −0.5 | 0.1 |
| volume | 6.5 | 3.9 |
| Lambda |  |  |
| initial | 20.8 | 21.1 |
| 1 week at 70 C. | 26.2 | 24.9 |
| 3 weeks at 70 C. | 27.8 | 26.9 |
| Fire test BS 4735 |  |  |
| flame spread (in mm) | 23.4 | 26.0 |
| time to extinguish (in sec) | 22.0 | 33.0 |
| burning rate (in mm/sec) | 1.07 | 0.79 |

These results show that polyurethane foam according to the present invention shows improved dimensional stability, improved thermal insulation ageing, improved fire performance, more resistance to deformation under load and improved compression strength as compared to a conventional polyurethane foam.

We claim:

1. Polyol compositions, prepared by the process comprising the oxyalkylation of at least one initiator, characterized in that at least one of the initiators is a compound corresponding to formula (I)

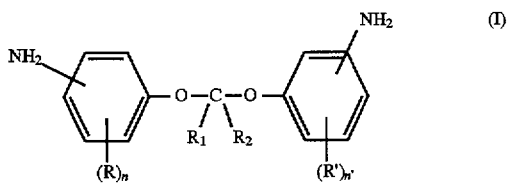

wherein:

R and R' each independently represent an alkyl chain of 1 to 10 carbon atoms, which may be branched, and which may be partially or fully fluorinated; n and n' each independently represent an integer of from 0 to 4;

the R, respectively R' substituents may be the same or different when n, respectively n' is greater than 1;

$R_1$ and $R_2$ independently represent hydrogen or an alkyl chain of 1 to 5 carbon atoms, which may be branched, and which may be partially or fully fluorinated, or $R_1$ and $R_2$, together represent an alkylene chain of 2 to 6 carbon atoms, which may be substituted by alkyl groups and which may be partially or fully fluorinated;

and wherein the amino substituents are situated in ortho, meta or para position with regard to the oxy substituent.

2. Method for preparing a polyol composition comprising the oxyalkylation of at least one initiator, characterized in that at least one of the initiators is a compound corresponding to Formula (I)

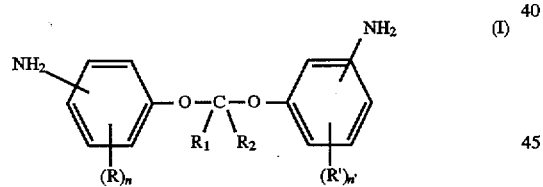

wherein:

R and R' each independently represent an alkyl chain of 1 to 10 carbon atoms, which may be branched, and which may be partially or fully fluorinated;

n and n' each independently represent an integer of from 0 to 4;

the R, respectively R' substituents may be the same or different when n, respectively n' is greater than 1;

$R_1$ and $R_2$ independently represent hydrogen or an alkyl chain of 1 to 5 carbon atoms, which may be branched, and which may be partially or fully fluorinated, or $R_1$ and $R_2$ together represent an alkylene chain of 2 to 6 carbon atoms, which may be substituted by alkyl groups and which may be partially or fully fluorinated;

and wherein the amino substituents are situated in ortho, meta or para position with regard to the oxy substituent.

3. Modified diaminodiphenylmethane compounds prepared by the process comprising reacting a compound of formula (I) with aniline and formaldehyde

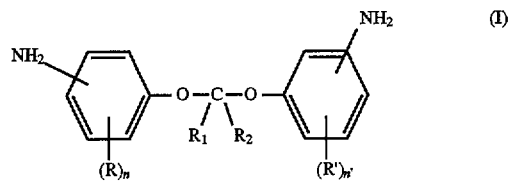

wherein:

R and R' each independently represent an alkyl chain of 1 to 10 carbon atoms, which may be branched, and which may be partially or fully fluorinated;

n and n' each independently represent an integer of from 0 to 4;

the R, respectively R' substituents may be the same or different when n, respectively n' is greater than 1;

$R_1$ and $R_2$ independently represent hydrogen or an alkyl chain of 1 to 5 carbon atoms, which may be branched, and which may be partially or fully fluorinated, or $R_1$ and $R_2$ together represent an alkylene chain of 2 to 6 carbon atoms, which may be substituted by alkyl groups and which may be partially or fully fluorinated;

and wherein the amino substituents are situated in ortho, meta or para position with regard to the oxy substituent.

4. Method for preparing a modified diaminodiphenylmethane compound by reacting a compound of formula (I) with aniline and formaldehyde

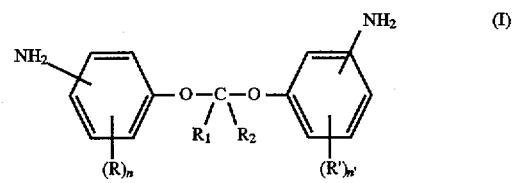

wherein:

R and R' each independently represent an alkyl chain of 1 to 10 carbon atoms, which may be branched, and which may be partially or fully fluorinated;

n and n' each independently represent an integer of from 0 to 4, the R, respectively R' substituents may be the same or different when n, respectively n' is greater than 1;

$R_1$ and $R_2$ independently represent hydrogen or an alkyl chain of 1 to 5 carbon atoms, which may be branched, and which may be partially or fully fluorinated, or $R_1$ and $R_2$ together represent an alkylene chain of 2 to 6 carbon atoms, which may be substituted by alkyl groups and which may be partially or fully fluorinated;

and wherein the amino substituents are situated in ortho, meta or para position with regard to the oxy substituent.

5. Polyol compositions prepared by the process comprising the oxyalkylation of at least one initiator, characterised in that at least one of the initiators is a modified diaminodiphenylmethane compound as defined in claim 3.

6. Method for preparing a polyol composition comprising the oxyalkylation of at least one initiator, characterised in that at least one of the initiators is a modified diaminodiphenylemethane compound as defined in claim 3.

7. Polyisocyanate composition prepared by the process comprising the phosgenation of a modified diaminodiphenylmethane compound as defined in claim 3.

8. Method for preparing a polyisocyanate composition comprising the phosgenation of a modified diaminodephenylmethane compound as defined in claim 3.

9. Method for preparing a polyurethane material comprising reacting a polyol composition with a polyisocyanate composition, characterised in that the polyol composition comprises a polyol as defined in claim 1.

10. Polyurethane prepared by the process comprising reacting a polyol composition with a polyisocyanate composition, characterized in that the polyol composition comprises a polyol as defined in claim 1.

11. Method for preparing a polyurethane material comprising reacting a polyol with a polyisocyanate in the presence of a chain extender, characterized in that the chain extender is a compound corresponding to formula (I)

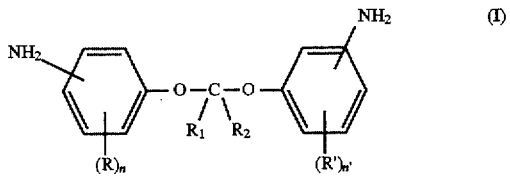

wherein:

R and R' each independently represent an alkyl chain of 1 to 10 carbon atoms, which may be branched, and which may be partially or fully fluorinated;

n and n' each independently represent an integer from 0 to 4, the R, respectively R' substituents may be the same or different when n, respectively n' is greater than 1;

$R_1$ and $R_2$ independently represent hydrogen or an alkyl chain of 1 to 5 carbon atoms, which may be branched, and which may be partially or fully fluorinated, or $R_1$ and $R_2$ together represent an alkylene chain of 2 to 6 carbon atoms, which may be substituted by alkyl groups and which may be partially of fully fluorinated; and wherein the amino substituents are situated in ortho, meta or para position with regard to the oxy substituent; with the exception of bis-(2- and 3- and 4-aminophenoxy) methane.

12. Method for preparing a polyurethane material according to claim 11 wherein at least one of the R and R' substituents represents an alkyl chain or wherein $R_{1\ and\ R2}$ together represent an alkylene chain.

13. Method for preparing a polyurethane material comprising reacting a polyol with a polyisocyanate in the presence of a chain extender, characterised in that the chain extender is a modified diaminodiphenylmethane compound as defined in claim 3.

14. Polyol composition containing a chain extender in an amount of from 0.1 to 20 parts by weight based on the total composition, characterized in that the chain extender is a modified diaminodiphenylmethane compound as defined in claim 3.

15. Method for preparing a polyurethane material comprising reacting a polyol composition with a polyisocyanate composition, characterized in that the polyol composition comprises a polyol as defined in claim 5.

16. Method for preparing a polyurethane material comprising reacting a polyol composition with a polyisocyanate composition, characterized in that the polyisocyanate composition comprises a product as defined in claim 7.

17. Method for preparing a polyurethane material comprising reacting a polyol composition with a polyisocyanate composition, characterized in that the polyol composition is prepared by the process comprising the oxyalkylation of at least one initiator, characterised in that at least one of the initiators is a compound corresponding to formula (I)

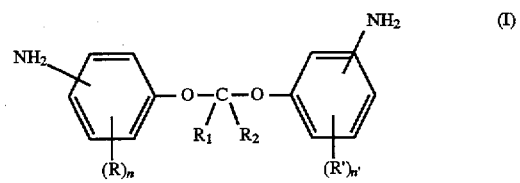

wherein:

R and R' each independently represent an alkyl chain of 1 to 10 carbon atoms, which may be branched, and which may be partially or fully fluorinated;

n and n' each independently represent an integer of from 0 to 4;

the R, respectively R' substituents may be the same or different when n, respectively n' is greater than 1;

$R_1$ and $R_2$ independently represent hydrogen or an alkyl chain of 1 to 5 carbon atoms, which may be branched, and which may be partially or fully fluorinated, or $R_1$ and $R_2$ together represent an alkylene chain of 2 to 6 carbon atoms, which may be substituted by alkyl groups and which may be partially or fully fluorinated;

and wherein the amino substituents are situated in ortho, meta or para position with regard to the oxy substituent; and the polyisocyanate composition comprises a product as defined in claim 7.

18. Method for preparing a polyurethane material comprising reacting a polyol composition with a polyisocyanate composition, characterized in that the polyol composition comprises a polyol as defined in claim 1 and the polyisocyanate composition comprises bis-(3 or 4-isocyanatophenoxy) methane.

19. Method for preparing a polyurethane material comprising reacting a polyol composition with a polyisocyanate composition, wherein the polyol composition is prepared by the process comprising the oxyalkylation of at least one initiator, wherein at least one of the initiators is a modified diaminodiphenylmethane compound prepared by the process comprising reacting a compound of formula (I) with aniline and formaldehyde

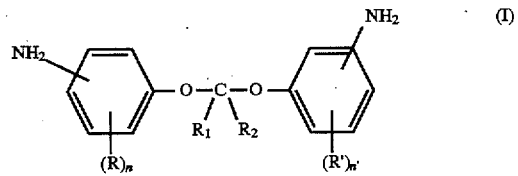

wherein:

R and R' each independently represent an alkyl chain of 1 to 10 carbon atoms, which may be branched, and which may be partially or fully fluorinated;

n and n' each independently represent an integer of from 0 to 4;

the R, respectively R' substituents may be the same or different when n, respectively n' is greater than 1;

$R_1$ and $R_2$ independently represent hydrogen or an alkyl chain of 1 to 5 carbon atoms, which may be branched, and which may be partially or fully fluorinated, or $R_1$ and $R_2$ together represent an alkylene chain of 2 to 6 carbon atoms, which may be substituted by alkyl groups and which may be partially or fully fluorinated;

and wherein the amino substituents are situated in ortho, meta or para position with regard to the oxy substituent; and the polyisocyanate composition comprises a product as defined in claim 7.

20. Method for preparing a polyurethane material comprising reacting a polyol composition with a polyisocyanate composition, wherein the polyol composition comprises a polyol as defined in claim 1 and the polyisocyanate composition comprises bis(3- or 4-isocyanatophenoxy) methane.

21. Polyurethane prepared by the process comprising reacting a polyol composition with a polyisocyanate composition, characterized in that the polyol composition comprises a polyol as defined in claim 6.

22. Polyurethane prepared by the process comprising reacting a polyol composition with a polyisocyanate composition, characterized in that the polyisocyanate composition comprises a product as defined in claim 7.

23. Polyurethane prepared by the process comprising reacting a polyol composition with a polyisocyanate composition, wherein said polyol composition is prepared by the process comprising the oxyalkylation of at least one initiator, wherein at least one or the initiators is a modified diaminodiphenylmethane compound prepared by the process comprising reacting a compound of formula (I) with aniline and formaldehyde

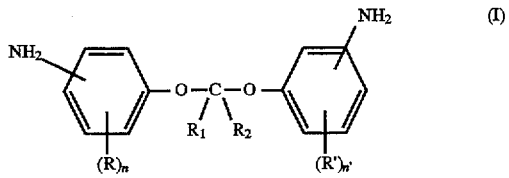

wherein:
- R and R' each independently represent an alkyl chain of 1 to 10 carbon atoms, which may be branched, and which may be partially or fully fluorinated;
- n and n' each independently represent an integer of from 0 to 4;
- the R, respectively R' substituents may be the same or different when n, respectively n' is greater than 1;
- $R_1$ and $R_2$ independently represent hydrogen or an alkyl chain of 1 to 5 carbon atoms, which may be branched, and which may be partially or fully fluorinated, or $R_1$ and $R_2$ together represent an alkylene chain of 2 to 6 carbon atoms, which may be substituted by alkyl groups and which may be partially or fully fluorinated;
- and wherein the amino substituents are situated in ortho, meta or para position with regard to the oxy substituent; and the polyisocyanate composition comprises a product as defined in claim 7.

24. Polyurethane prepared by the process comprising reacting a polyol composition with a polyisocyanate composition, characterized in that the polyol composition comprises a polyol as defined in claim 1 and the polyisocyanate composition comprises bis(3- or 4-isocyanatophenoxy) methane.

25. Polyurethane prepared by the process comprising reacting a polyol composition with a polyisocyanate composition, wherein said polyol composition is prepared by the process comprising the oxyalkylation of at least one initiator, characterized in that at least one of the initiators is a compound of formula (I)

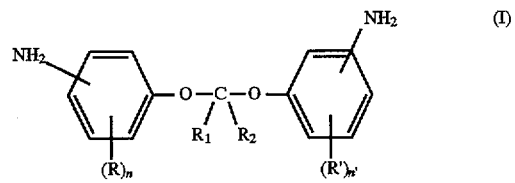

wherein:
- R and R' each independently represent an alkyl chain of 1 to 10 carbon atoms, which may be branched, and which may be partially or fully fluorinated;
- n and n' each independently represent an integer of from 0 to 4;
- the R, respectively R' substituents may be the same or different when n, respectively n' is greater than 1;
- $R_1$ and $R_2$ independently represent hydrogen or an alkyl chain of 1 to 5 carbon atoms, which may be branched, and which may be partially or fully fluorinated, or $R_1$ and $R_2$ together represent an alkylene chain of 2 to 6 carbon atoms, which may be substituted by alkyl groups and which may be partially or fully fluorinated;
- and wherein the amino substituents are situated in ortho, meta or para position with regard to the oxy substituent; and the polyisocyanate composition comprises a product as defined in claim 7.

26. Polyurethane prepared by the process comprising reacting a polyol composition with a polyisocyanate composition, wherein the polyol composition comprises a polyol as defined in claim 5 and the polyisocyanate composition comprises bis(3- or 4-isocyanatophenoxy) methane.

* * * * *